United States Patent
Yagi et al.

(10) Patent No.: US 9,351,784 B2
(45) Date of Patent: May 31, 2016

(54) SHAFT FOR ABLATION CATHETER WITH BALLOON

(75) Inventors: Takahiro Yagi, Otsu (JP); Motoki Takaoka, Otsu (JP); Akinori Matsukuma, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 970 days.

(21) Appl. No.: 13/260,807

(22) PCT Filed: Mar. 30, 2010

(86) PCT No.: PCT/JP2010/055632
§ 371 (c)(1),
(2), (4) Date: Sep. 28, 2011

(87) PCT Pub. No.: WO2010/113914
PCT Pub. Date: Oct. 7, 2010

(65) Prior Publication Data
US 2012/0065633 A1    Mar. 15, 2012

(30) Foreign Application Priority Data

Mar. 31, 2009  (JP) ................................. 2009-085005

(51) Int. Cl.
*A61B 18/04* (2006.01)
*A61B 18/14* (2006.01)
*A61B 18/00* (2006.01)

(52) U.S. Cl.
CPC ............. *A61B 18/04* (2013.01); *A61B 18/1492* (2013.01); *A61B 2018/0022* (2013.01);
(Continued)

(58) Field of Classification Search
CPC .................... A61B 18/04; A61B 2018/00577; A61B 2018/0022; A61B 2018/00404; A61B 18/1492; A61B 2018/00166; A61B 2018/00642; A61B 2018/00702; A61B 2018/00791; A61B 2018/0046; A61B 2018/1472
USPC ............. 606/20, 21, 22, 28, 42; 607/105, 113
See application file for complete search history.

(56) References Cited

U.S. PATENT DOCUMENTS 5,704,934 A * 1/1998 Neuwirth et al. ............... 606/28
6,290,696 B1 * 9/2001 Lafontaine ..................... 606/21
(Continued)

FOREIGN PATENT DOCUMENTS

EP      1384445      1/2004
JP      7184919 A    7/1995
(Continued)

OTHER PUBLICATIONS

International Application Serial No. PCT/JP2010/055632, International Search Report mailed Jun. 29, 2010, 2 pgs.
(Continued)

*Primary Examiner* — Christopher D Koharski
*Assistant Examiner* — Pamela M Bays
(74) *Attorney, Agent, or Firm* — RatnerPrestia

(57) ABSTRACT

The stirring efficiency of a heating liquid which is supplied to the balloon of a balloon-equipped ablation catheter is increased to quickly uniformize the surface temperature of the balloon, and air is prevented from remaining in the balloon-equipped ablation catheter to enhance the safety of treatment which uses the balloon-equipped ablation catheter. A shaft for a balloon-equipped ablation catheter, consisting of a single pipe, wherein the shaft has two lumens which communicate from the distal end to the proximal end of the shaft, a first lumen being a guide wire passage lumen which is provided in order to allow a guide wire to pass therethrough, the second lumen being a liquid supply lumen which is provided in order to supply liquid to the inside of the balloon of the balloon-equipped ablation catheter.

2 Claims, 10 Drawing Sheets

(52) U.S. Cl.
 CPC ............... *A61B2018/00166* (2013.01); *A61B 2018/00404* (2013.01); *A61B 2018/00577* (2013.01); *A61B 2018/00642* (2013.01); *A61B 2018/00702* (2013.01); *A61B 2018/00791* (2013.01); *A61B 2018/046* (2013.01); *A61B 2018/1472* (2013.01)

(56) References Cited

U.S. PATENT DOCUMENTS

2002/0156469 A1\* 10/2002 Yon et al. ..................... 606/21
2003/0065371 A1    4/2003 Satake
2004/0172112 A1\*  9/2004 Cioanta ................. A61F 7/12
                                                              607/105
2008/0039790 A1    2/2008 Hasebe

FOREIGN PATENT DOCUMENTS

| | | |
|---|---|---|
| JP | 2002113107 A | 4/2002 |
| JP | 2003102850 A | 4/2003 |
| JP | 2003524506 A | 8/2003 |
| JP | 2005185661 A | 7/2005 |
| JP | 2005245930 A | 9/2005 |
| JP | 2007229095 A | 9/2007 |
| JP | 2009261581 A | 11/2009 |
| WO | 9902096 | 1/1999 |

OTHER PUBLICATIONS

Russian Office Action mailed Oct. 17, 2012 for Russian Application No. 20111143737/14(065642).

\* cited by examiner $La = L1 + L2 + L3 + L4$

Area of liquid supplying lumen region

A-A' cross-section

SHAFT FOR ABLATION CATHETER WITH BALLOON

CROSS-REFERENCE TO RELATED APPLICATIONS

This application is the U.S. National Phase application of PCT International Application No. PCT/JP2010/055632, filed Mar. 30, 2010, and claims priority to Japanese Patent Application No. 2009-085005, filed Mar. 31, 2009, the disclosures of which PCT and priority applications are incorporated herein by reference in their entirely for all purposes.

TECHNICAL FIELD

The present invention relates to a shaft for an ablation catheter with a balloon.

BACKGROUND OF THE INVENTION

Catheter ablation is a treatment method by inserting an ablation catheter into a cardiac chamber and applying heat between a tip electrode and a counter electrode plate to ablate and remove a myocardial tissue causing an arrhythmia. The catheter ablation is useful mainly for treatment of tachyarrythmias such as a paroxysmal supraventricular tachycardia, an atrial tachycardia, an atrial flutter, and a paroxysmal ventricular tachycardia, and recently, an ablation catheter with a balloon having a balloon at the tip of a catheter tube is used (Patent Literatures 1 and 2).

The ablation catheter with a balloon is a medical device of expanding a balloon fixed to the tip of a catheter by a liquid for heating and heating the liquid for heating by a radio-frequency current supplied from a radio-frequency generator to ablate the entire myocardial tissue contacting the surface of the balloon. The temperature of the balloon is adjusted, for example, by a vibration applying device, which applies a vibration to the liquid for heating filled in the balloon, and is controlled by a temperature sensor arranged in the balloon.

As a means for uniforming the temperature of the liquid in the balloon, Patent Literature 1 discloses an ablation catheter with a balloon having a double-pipe structure including an outer cylinder shaft and an inner cylinder shaft and mixing the liquid in the balloon by vibrating the liquid supplied in the balloon and in a space between the outer cylinder shaft and the inner cylinder shaft.

PATENT LITERATURE

Patent Literature 1: Japanese Patent No. 3607231
Patent Literature 2: Japanese Patent No. 3892438

SUMMARY OF THE INVENTION

In the ablation catheter with a balloon disclosed in Patent Literature 1, since the liquid for heating supplied in the balloon and in the space between the outer cylinder shaft and the inner cylinder shaft is not perfused smoothly, it takes a long time to uniform the surface temperature of the balloon, and a variation occurs in the surface temperature of the balloon, which causes concern about increase in burden on a patient and decrease in treatment accuracy.

Also, since the liquid for heating is not perfused smoothly, air bubbles are attached to the balloon, the inner surface of the outer cylinder shaft, and the outer surface of the inner cylinder shaft even when the liquid is supplied in the balloon and in the space between the outer cylinder shaft and the inner cylinder shaft before treatment to deflate the ablation catheter with a balloon, and complete deflation is difficult. Air remaining in the balloon and the like has an adverse effect on uniforming the surface temperature of the balloon and may be mixed in a blood vessel of the patient in a case where the balloon is damaged during the treatment, and thus complete deflation of the ablation catheter with a balloon is required in terms of assurance of the patient's safety.

The present invention can increase a mixing efficiency of a liquid for heating to be supplied to a balloon of an ablation catheter with a balloon to uniform a surface temperature of the balloon quickly, and can prevent air from remaining in the ablation catheter with a balloon to enhance safety of treatment using the ablation catheter with a balloon.

As a result of concerted study directed toward solving the aforementioned problem, the present inventors discovered the following (1) to (4).

(1) A shaft for an ablation catheter with a balloon formed of a single pipe comprising two lumens communicating from a distal end to a proximal end, wherein the first lumen is a guidewire passing lumen provided to allow a guidewire to pass therethrough, and the second lumen is a liquid supplying lumen provided to supply a liquid to an interior of a balloon of the ablation catheter with a balloon.
(2) The shaft for an ablation catheter with a balloon according to the above (1), wherein a value (La/Li) derived by dividing a length (La) of an outline of a shape of the liquid supplying lumen in a cross-section perpendicular to a longitudinal direction of the single pipe by a length (Li) of a circumference of a circle having an equal area to an area of a liquid supplying lumen region surrounded by the outline is 1 to 2.3, and the area of the liquid supplying lumen region is 2.0 to 4.5 mm$^2$.
(3) The shaft for an ablation catheter with a balloon according to the above (1) or (2), wherein a value (La/Li) derived by dividing a length (La) of an outline of a shape of the liquid supplying lumen in a cross-section perpendicular to a longitudinal direction of the single pipe by a length (Li) of a circumference of a circle having an equal area to an area of a liquid supplying lumen region surrounded by the outline is 1 to 1.8.
(4) An ablation catheter system with a balloon comprising the shaft for an ablation catheter with a balloon according to any one of the above (1) to (3).

With the present invention, at the time of treatment with use of an ablation catheter with a balloon, it is possible to allow a liquid for heating to be supplied to an interior of a balloon to pass through a liquid supplying lumen provided in a shaft for an ablation catheter with a balloon more smoothly, which enables to increase a mixing efficiency of the liquid for heating. Also, with the present invention, it can take a short time to uniform a surface temperature of the balloon to decrease a burden on a patient, and air can be prevented from remaining in the ablation catheter with a balloon to achieve enhanced safety and a high treatment effect.

Figure 1:
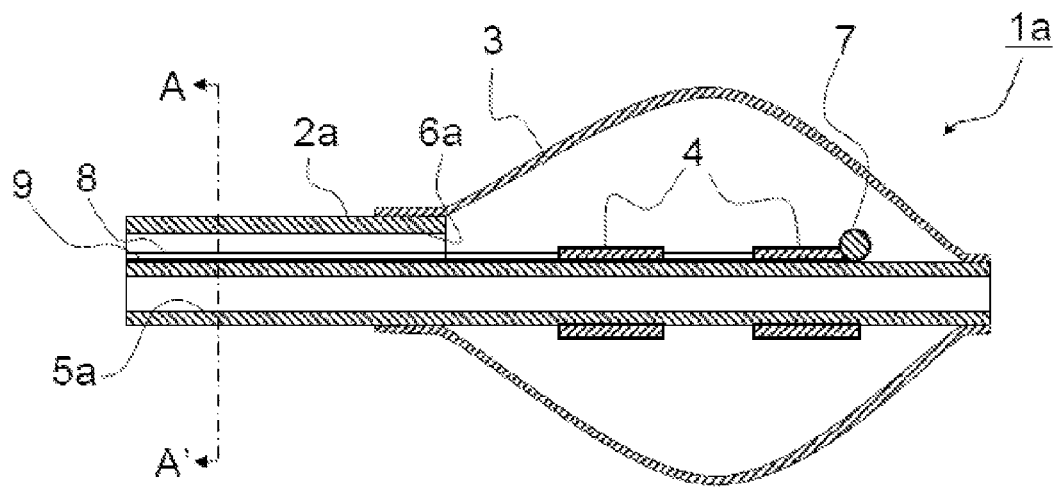
FIG. 1 is a schematic view showing a cross-section horizontal with a longitudinal direction of a balloon portion of an ablation catheter with a balloon having a shaft for an ablation catheter with a balloon according to a first embodiment of the present invention.

DESCRIPTION OF PREFERRED
EMBODIMENTS OF THE INVENTION

Preferred embodiments of the present invention will be described below with reference to the accompanying drawings, but the present invention is not limited to these embodiments. Like reference characters designate similar or identical parts throughout the several views thereof, and duplicate explanation is omitted. Also, the ratio in the drawings does not necessarily correspond to an actual ratio.

A shaft for an ablation catheter with a balloon according to an embodiment of the present invention is a shaft for an ablation catheter with a balloon formed of a single pipe and includes two lumens communicating from a distal end to a proximal end, wherein the first lumen is a guidewire passing lumen provided to allow a guidewire to pass therethrough, and the second lumen is a liquid supplying lumen provided to supply a liquid to an interior of a balloon of the ablation catheter with a balloon.

Figure 2:
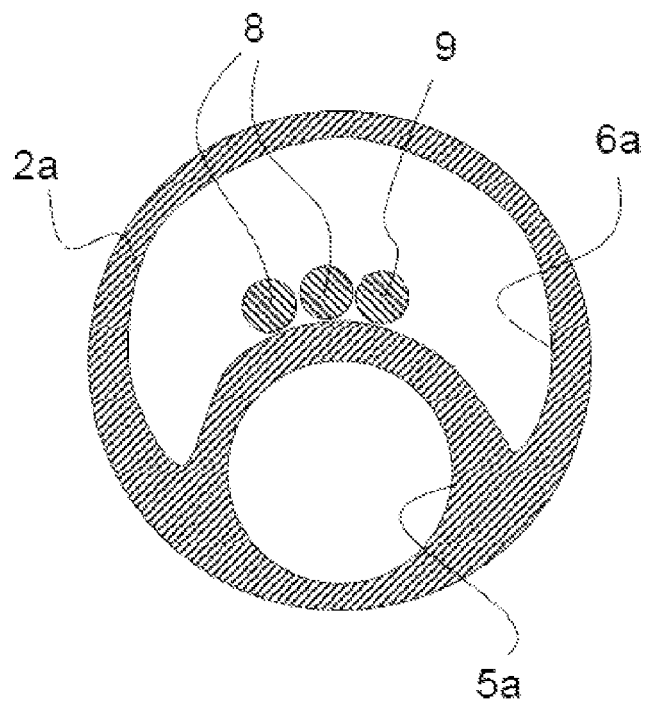
FIG. 2 is a schematic view showing a cross-section perpendicular to the longitudinal direction of the shaft for an ablation catheter with a balloon according to the first embodiment of the present invention.

FIG. 1 is a schematic view showing a cross-section horizontal with a longitudinal direction of a balloon portion of an ablation catheter with a balloon having a shaft for an ablation catheter with a balloon according to a first embodiment of the present invention. FIG. 2 is a schematic view showing a cross-section perpendicular to the longitudinal direction of the shaft for an ablation catheter with a balloon according to the first embodiment of the present invention.

A shaft for an ablation catheter with a balloon 2a of the ablation catheter with a balloon whose balloon portion 1a is shown in FIG. 1 is formed of a single pipe. A balloon 3 is attached to a front side of the shaft for an ablation catheter with a balloon 2a. Also, the shaft for an ablation catheter with a balloon 2a includes a guidewire passing lumen 5a that does not communicate with an interior of the balloon 3 and penetrates a shaft for an ablation catheter with a balloon 2 to a front end and a liquid supplying lumen 6a that communicates with the interior of the balloon 3.

An electrode 4 is fixed to the shaft for an ablation catheter with a balloon 2a in the interior of the balloon 3. A temperature sensor 7 for measuring a temperature in the balloon is fixed to the electrode 4. A radio-frequency carrying lead wire 8 connected to the electrode 4 and a temperature sensor lead wire 9 connected to the temperature sensor 7 pass through the liquid supplying lumen 6a as shown in FIG. 2, which shows the cross-section A-A' in FIG. 1.

"The single pipe" means a tube body that is formed of one tube or in which plural tubes contact without sliding with one another.

Materials for the plural tubes constituting the signal pipe may be the same as or different from one another.

Figure 3:
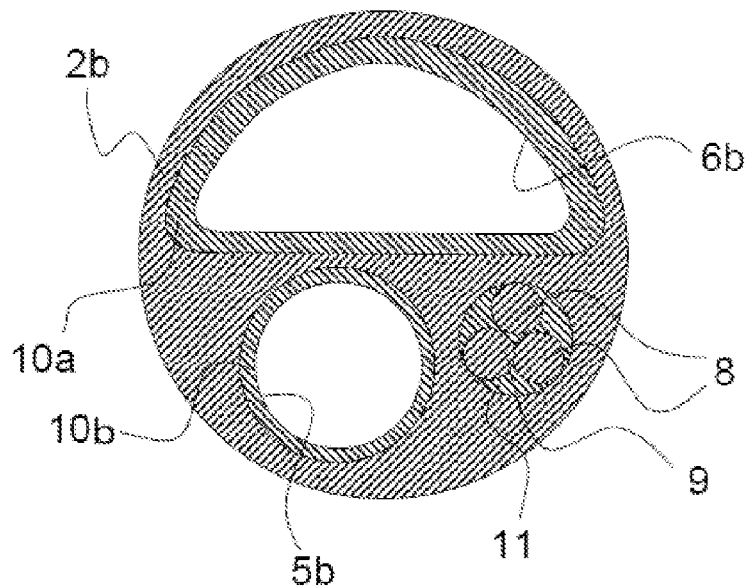
FIG. 3 is a schematic view showing a cross-section perpendicular to a longitudinal direction of a shaft for an ablation catheter with a balloon according to a second embodiment of the present invention.

FIG. 3 is a schematic view showing a cross-section perpendicular to a longitudinal direction of a shaft for an ablation catheter with a balloon constituted by plural tubes according to a second embodiment of the present invention.

In a shaft for an ablation catheter with a balloon 2b shown in FIG. 3, tubes 10a and 10b for forming layer structures on an inner surface of a guidewire passing lumen 5b and an inner surface of a liquid supplying lumen 6b and an embedded tube 11 contact without sliding with one another.

Into the embedded tube 11 may be inserted the lead wire 8 and the temperature sensor lead wire 9 collectively, as shown in FIG. 3.

Figure 4:
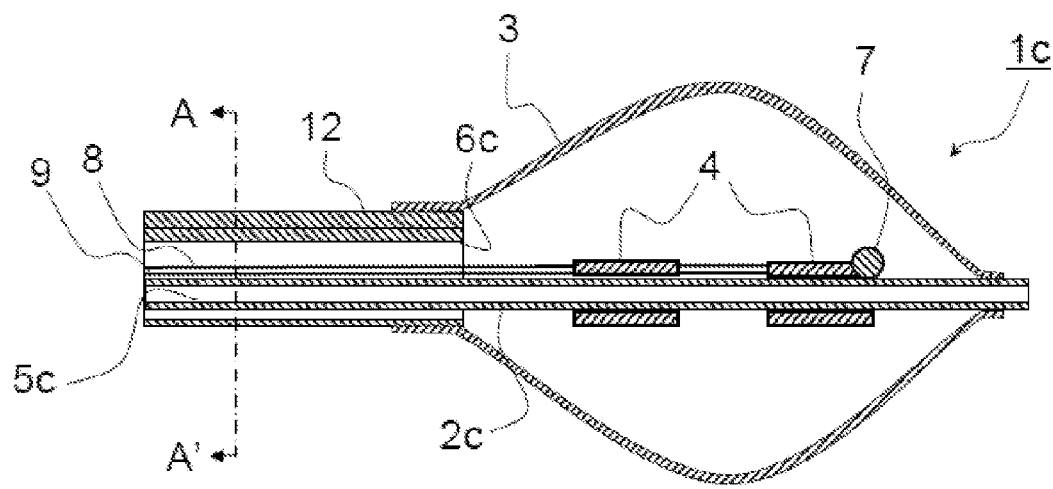
FIG. 4 is a schematic view showing a cross-section horizontal with a longitudinal direction of a balloon portion of an ablation catheter with a balloon having a shaft for an ablation catheter with a balloon according to a third embodiment of the present invention.
Figure 5:
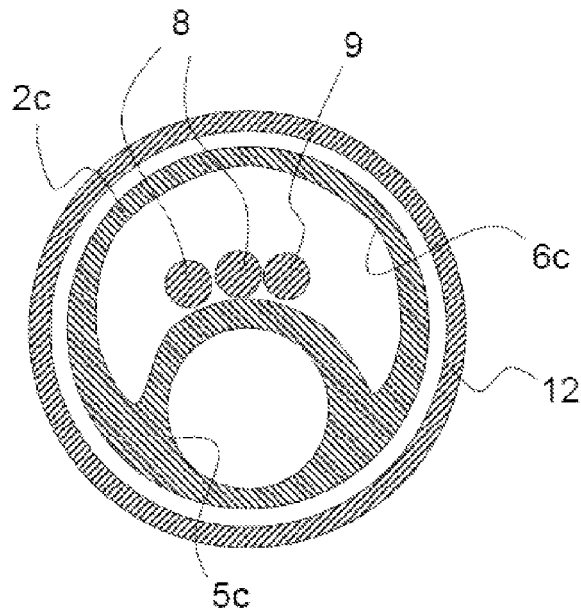
FIG. 5 is a schematic view showing a cross-section perpendicular to the longitudinal direction of the shaft for an ablation catheter with a balloon according to the third embodiment of the present invention.

FIG. 4 is a schematic view showing a cross-section horizontal with a longitudinal direction of a balloon portion of an ablation catheter with a balloon having a shaft for an ablation catheter with a balloon according to a third embodiment of the present invention. FIG. 5 is a schematic view showing a cross-section perpendicular to the longitudinal direction of the shaft for an ablation catheter with a balloon according to the third embodiment of the present invention.

A shaft for an ablation catheter with a balloon 2c of the ablation catheter with a balloon whose balloon portion 1c is shown in FIG. 4 is formed of a single pipe and includes a guidewire passing lumen 5c that does not communicate with the interior of the balloon 3 and penetrates the shaft for an ablation catheter with a balloon 2c to a front end and a liquid supplying lumen 6c that communicates with the interior of the balloon 3.

The shaft for an ablation catheter with a balloon 2c is inserted into an outer cylinder shaft 12 to constitute a double-cylinder shaft in which the shaft for an ablation catheter with a balloon 2c is slidable in a longitudinal direction. A rear portion of the balloon 3 is fixed to a front portion in a longitudinal direction of the outer cylinder shaft 12 while a front portion of the balloon 3 is fixed to a front end in the longitudinal direction of the shaft for an ablation catheter with a balloon 2c.

The electrode 4 is fixed to the shaft for an ablation catheter with a balloon 2c in the interior of the balloon 3. The temperature sensor 7 for measuring a temperature in the balloon is fixed to the electrode 4. The radio-frequency carrying lead wire 8 connected to the electrode 4 and the temperature sensor lead wire 9 connected to the temperature sensor 7 pass through the liquid supplying lumen 6c as shown in FIG. 5, which shows the cross-section A-A' in FIG. 4.

A material for the shafts for an ablation catheter with a balloon 2a, 2b, and 2c, the tubes 10a and 10b, and the embedded tube 11 is preferably a flexible material with excellent antithrombogenicity such as a polyamide resin represented by nylon 11 or nylon 12, polyamide elastomer, polyolefin represented by polypropylene or polyethylene, polyester represented by polyethylene terephthalate, polyurethane, or vinyl chloride.

A material for the balloon 3 is preferably a flexible material with excellent antithrombogenicity and is more preferably a polyurethane polymeric material.

Examples of the polyurethane polymeric material include thermoplastic polyether urethane, polyether polyurethane urea, fluorine polyether urethane urea, a polyether polyurethane urea resin, and polyether polyurethane urea amide.

The film thickness of the balloon 3 is preferably 20 to 150 microns and is more preferably 20 to 100 microns from a viewpoint of close contact with an affected tissue.

As for the diameter of the balloon 3, an appropriate diameter has only to be selected depending on the target to be ablated, and the diameter is preferably 20 to 40 mm in a case of treatment of an arrhythmia, for example.

The shape of the balloon 3 is preferably a tapered conical outer shape and is more preferably a spherical shape.

Examples of a method for fixing the electrode 4 to the shaft for an ablation catheter with a balloon 2a, 2b, or 2c include caulking, adhesive, welding, and a heat shrinkable tube.

The balloon is heated by supplying one or plural electrodes 4 fixed to the interior of the balloon 3 with radio-frequency power by a radio-frequency generator. Meanwhile, a unipolar method, in which the balloon is heated by supplying the radio-frequency power by the radio-frequency generator between one electrode 4 fixed to the interior of the balloon 3 and a counter electrode plate attached to a surface of a patient's body, may be adopted.

The shape of the electrode 4 is not particularly limited and is preferably a tubular shape such as a coiled shape or a cylindrical shape.

The diameter of an electric wire of the coiled electrode is preferably 0.05 to 0.5 mm from a viewpoint of practicality.

A material for the electrode 4 is preferably a highly conductive metal.

Examples of the highly conductive metal include highly conductive metals such as silver, gold, platinum, and copper.

Examples of a method for fixing the temperature sensor 7 and the lead wire 8 to the electrode 4 include soldering, caulking, and welding.

Examples of the temperature sensor 7 include a thermocouple and a resistance-temperature detector.

The temperature sensor 7 is fixed to the shaft for an ablation catheter with a balloon 2a, 2b, or 2c, the electrode 4, or an inner surface of the balloon 3. Plural temperature sensors 7 may be fixed from a viewpoint of backup in a case of a failure of the temperature sensor.

The diameter of the lead wire 8 is not particularly limited and is preferably 0.05 to 0.8 mm from a viewpoint of practicality.

Examples of a material for the lead wire 8 include highly conductive electric wires such as copper, silver, gold, platinum, tungsten, and an alloy. The lead wire 8 is preferably provided with an electrical insulating protective coat such as a fluorine resin from a viewpoint of preventing short circuit, and it is more preferable to form a part of the lead wire 8, from which the electrical insulating protective coat has been stripped away, in a coiled shape and use the part as the electrode 4 from a viewpoint of dispensing with connection by soldering, caulking, or welding.

The diameter of the temperature sensor lead wire 9 is preferably 0.05 to 0.5 mm from a viewpoint of practicality.

When the temperature sensor 8 is a thermocouple, a material for the temperature sensor lead wire 9 is preferably the same material as that for the thermocouple, and examples of the material include copper and constantan when the temperature sensor 8 is a T-shaped thermocouple. On the other hand, when the temperature sensor 8 is a resistance-temperature detector, a material for the temperature sensor lead wire 9 is preferably a highly conductive electric wire such as copper, silver, gold, platinum, tungsten, or an alloy. Meanwhile, the temperature sensor lead wire 9 is preferably provided with an electrical insulating protective coat such as a fluorine resin from a viewpoint of preventing short circuit.

Also, in the shaft for an ablation catheter with a balloon according to an embodiment of the present invention, a value (La/Li) derived by dividing a length (La) of an outline of a shape of the liquid supplying lumen in a cross-section perpendicular to a longitudinal direction of the single pipe by a length (Li) of a circumference of a circle having an equal area to an area of a liquid supplying lumen region surrounded by the outline is 1 to 2.3, and the area of the liquid supplying lumen region is 2.0 to 4.5 mm$^2$.

Figure 6:
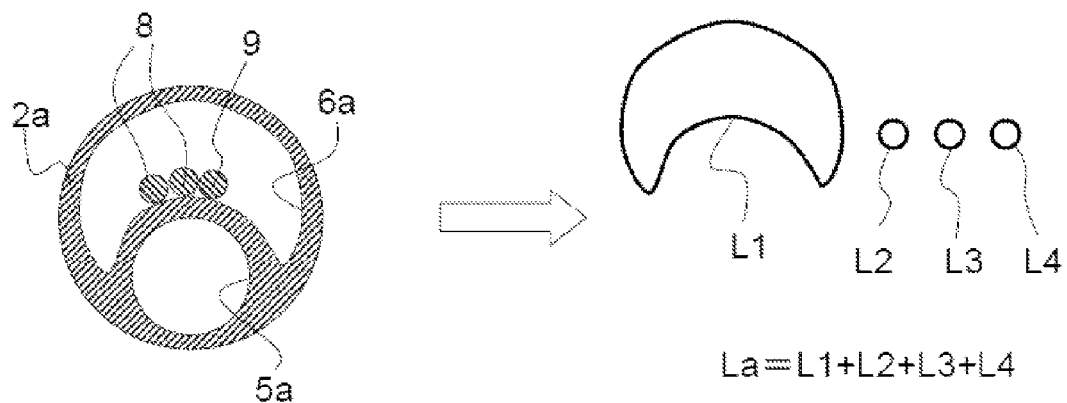
FIG. 6 illustrates a length (La) of an outline of a shape of a liquid supplying lumen in the cross-section perpendicular to the longitudinal direction of the shaft for an ablation catheter with a balloon according to the first embodiment of the present invention.
Figure 7:
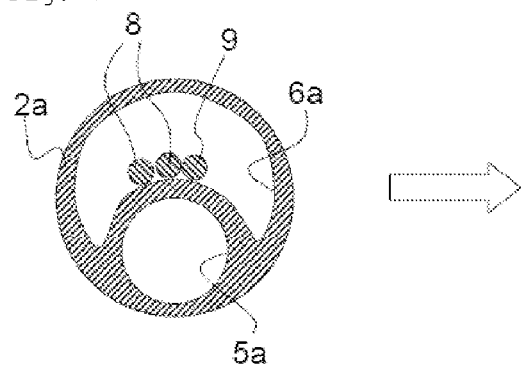
FIG. 7 illustrates an area of a liquid supplying lumen region surrounded by the outline of the shape of the liquid supplying lumen in the cross-section perpendicular to the longitudinal direction of the shaft for an ablation catheter with a balloon according to the first embodiment of the present invention.

FIG. 6 illustrates a length (La) of an outline of a shape of the liquid supplying lumen in a cross-section perpendicular to a longitudinal direction of the shaft for an ablation catheter with a balloon according to the first embodiment of the present invention. FIG. 7 illustrates an area of a liquid supplying lumen region surrounded by the outline of the shape of the liquid supplying lumen in the cross-section perpendicular to the longitudinal direction of the shaft for an ablation catheter with a balloon according to the first embodiment of the present invention.

The liquid for heating to be supplied to the interior of the balloon 3 passes through the liquid supplying lumen 6a. The outline of the shape of the liquid supplying lumen is L1, which is an inner circumference of the liquid supplying lumen 6a, L2 and L3, which are outer circumferences of the lead wires 8, and L4, which is an outer circumference of the temperature sensor lead wire 9, and "the length (La) of the outline of the shape of the liquid supplying lumen" refers to a value of a total length of L1, L2, L3, and L4.

Li refers to a length of a circumference of a circle having an equal area to the area of the liquid supplying lumen region surrounded by the outline of the shape of the liquid supplying lumen, that is, the area of the colored part shown on the right side of FIG. 7.

A value derived by dividing La by Li, that is, La/Li, is preferably 1 to 2.3 and is more preferably 1 to 1.8 from a viewpoint of allowing the liquid such as saline to pass more smoothly.

The area of the liquid supplying lumen region is preferably 2.0 to 4.5 mm$^2$ from a viewpoint of securing insertability of the ablation catheter with a balloon in the patient's body as well as allowing the liquid such as saline to pass more smoothly.

Further, an ablation catheter system with a balloon according to aspects of the present invention includes the shaft for an ablation catheter with a balloon according to aspects of the present invention.

Figure 8:
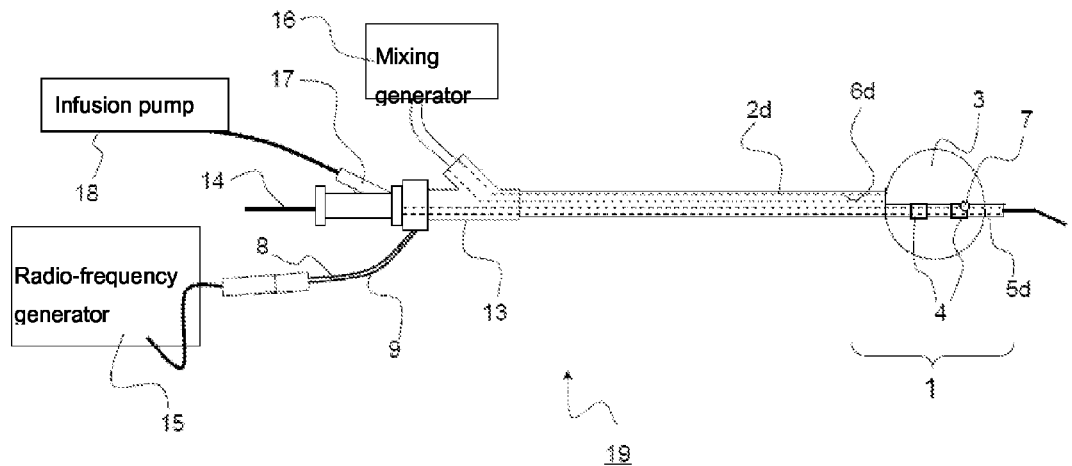
FIG. 8 is a schematic view showing an example of an ablation catheter system with a balloon according to an embodiment of the present invention.

FIG. 8 is a schematic view showing an example of an ablation catheter system with a balloon according to an embodiment of the present invention.

A shaft for an ablation catheter with a balloon 2d of an ablation catheter system with a balloon 19 shown in FIG. 8 is formed of a single pipe. The balloon 3 is attached to a front side of the shaft for an ablation catheter with a balloon 2d. Also, the shaft for an ablation catheter with a balloon 2d includes a guidewire passing lumen 5d that does not communicate with the interior of the balloon 3 and penetrates the shaft for an ablation catheter with a balloon 2d from a proximal end to a front end and a liquid supplying lumen 6d that penetrates the proximal end of the shaft for an ablation catheter with a balloon 2d and communicates with the interior of the balloon 3.

To a proximal side of the shaft for an ablation catheter with a balloon 2d is attached an operating portion 13, and the operating portion 13 has lumens respectively corresponding to the guidewire passing lumen 5d and the liquid supplying lumen 6d of the shaft for an ablation catheter with a balloon 2.

The liquid supplied to the interior of the balloon 3 and the like can be vibrated and mixed by a mixing generator 16 connected to the operating portion 13.

To the lumen of the operating portion 13 corresponding to the guidewire passing lumen 5d is connected a bifurcated connector 17 that bifurcates this lumen and communicates with the guidewire passing lumen 5d. A guidewire 14 passes through the guidewire passing lumen 5d via the bifurcated connector 17.

To the bifurcated connector 17 is connected an infusion pump 18 so that, even in a case where the shaft for an ablation catheter with a balloon 2d is inserted into a blood vessel of the patient, regurgitation of blood can be prevented by supplying the guidewire passing lumen 5d with glucose or saline from the infusion pump 18. Meanwhile, instead of using the infusion pump 18, the glucose or saline may be supplied to the guidewire passing lumen 5d by dripping with use of free fall such as a drip infusion.

The electrode 4 is fixed to the shaft for an ablation catheter with a balloon 2d in the interior of the balloon 3. The temperature sensor 7 for measuring a temperature in the balloon is fixed to the electrode 4. The radio-frequency carrying lead wire 8 connected to the electrode 4 and the temperature sensor lead wire 9 connected to the temperature sensor 7 pass through the shaft for an ablation catheter with a balloon 2d and the operating portion 13 and are connected to a radio-frequency generator 15.

The balloon 3 is heated by supplying the electrode 4 with radio-frequency power by the radio-frequency generator. At the same time as heating the balloon 3, the liquid in the balloon 3 and the like is vibrated and mixed by the mixing generator 16, a surface temperature of the balloon 3 is uniformed, and then the balloon 3 is brought into contact with the affected tissue for treatment.

Although a material for and shape of the guidewire 14 are not particularly limited, the guidewire 14 preferably has a tip shape that will not damage intracorporeal tissues at the time of being inserted into the patient's body.

The frequency of the radio-frequency power to be supplied from the radio-frequency generator 15 is preferably 100 kHz or higher from a viewpoint of preventing an electric shock of the patient.

Examples of the mixing generator 16 include a roller pump, a diaphragm pump, and a bellows pump, and the radio-frequency generator 15 and the mixing generator 16 are preferably integrated from a viewpoint of reducing the number of components of the ablation catheter system with a balloon according to aspects of the present invention.

An example of the bifurcated connector 17 is a Y-shaped connector.

The Y-shaped connector preferably has a valve mechanism from a viewpoint of preventing leakage of the liquid to be supplied to expand the balloon 3.

EXAMPLES

Hereinafter, specific examples of the shaft for an ablation catheter with a balloon will be described with reference to the drawings. It is to be noted that "a length" represents a length in a longitudinal direction.

Example 1

A shaft made of polyurethane having a length of 1000 mm and an outer diameter of 3.2 mm and having a guidewire passing lumen 5e with a cross-section perpendicular to a longitudinal direction of the shaft being a circle having a diameter of 1.1 mm, a liquid supplying lumen 6e with a cross-section perpendicular to the longitudinal direction of the shaft being a circle having a diameter of 1.6 mm, and a third lumen 20 with a cross-section perpendicular to the longitudinal direction of the shaft being a circle having a diameter of 1.1 mm was prepared by extrusion molding to obtain a shaft for an ablation catheter with a balloon 2e.

Figure 9:
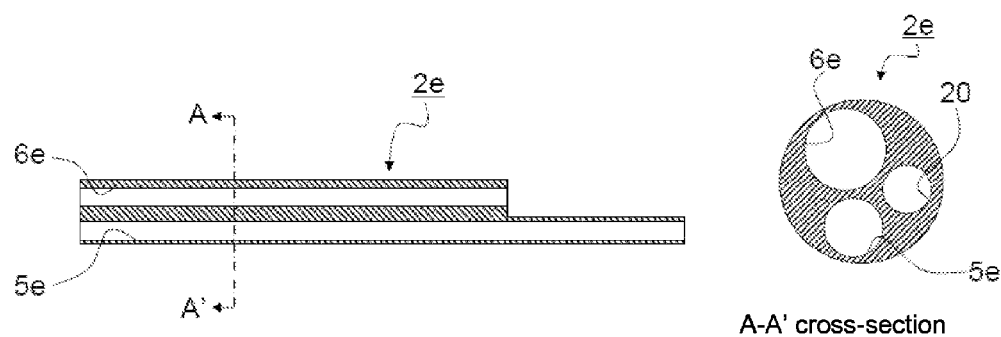
FIG. 9 is a schematic view showing a cross-section horizontal with and a cross-section perpendicular to a longitudinal direction of a front portion of a shaft for an ablation catheter with a balloon in EXAMPLE 1.

A part of a range including the liquid supplying lumen 6e and the third lumen 20 of the shaft for an ablation catheter with a balloon 2 from a front end of the shaft for an ablation catheter with a balloon 2e to a position 40 mm distanced in length from the front end was cut off to have the shape of the front portion shown in FIG. 9.

A copper wire plated with silver and undergoing FEP coating having a length of 1300 mm and a diameter of 0.72 mm was used as the lead wire 8, and a constantan wire undergoing FEP coating having a length of 1300 mm and a diameter of 0.29 mm was used as the temperature sensor lead wire 9.

The coat in a 150 mm range in length from one tip of the lead wire 8 was stripped away, the coat in a 3 mm range in length from one tip of the temperature sensor lead wire 9 was stripped away, and the tips from which the coats were stripped away were overlapped in a range of 1 mm in length of each wire and were fixed by soldering.

The temperature sensor lead wire 9 was inserted into the third lumen 20, and the fixed part of the tips of the lead wire 8 and the temperature sensor lead wire 9 was placed at a position 20 mm distanced in length from the front end of the shaft for an ablation catheter with a balloon 2e. With the position set as a starting point, the lead wire 8 was directly wound around the shaft for an ablation catheter with a balloon 2e and the temperature sensor lead wire 9 in a proximal direction of the ablation catheter with a balloon to form a coiled shape having a length in the longitudinal direction of 10 mm and use it as an electrode-cum-temperature sensor 21.

A remainder of the lead wire 8 after its part was formed in the coiled shape was inserted into the third lumen 20 along the temperature sensor lead wire 9, and the third lumen 20 into which the lead wire 8 and the temperature sensor lead wire 9 were inserted was sealed by filling epoxy adhesive.

The balloon 3 made of polyurethane formed in a spherical shape having a diameter of 25 mm and a thickness of 40 μm and having at both ends neck portions one having a length of 15 mm and an inner diameter of 3.2 mm and the other having a length of 15 mm and an inner diameter of 1.6 mm was prepared by dipping.

The neck portion of the balloon 3 having an inner diameter of 3.2 mm was thermally welded on an outer circumference of the front portion of the shaft for an ablation catheter with a balloon 2e, and the neck portion of the balloon 3 having an inner diameter of 1.6 mm was thermally welded so that the liquid supplying lumen 6e of the shaft for an ablation catheter with a balloon 2e would communicate with the interior of the balloon 3.

Figure 10:
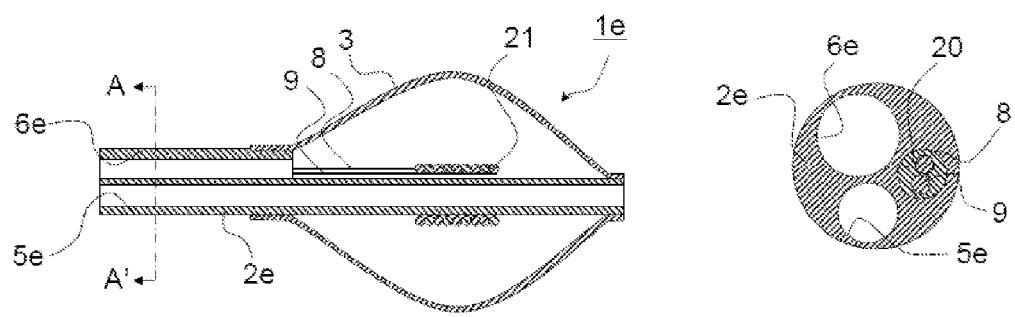
FIG. 10 is a schematic view showing a cross-section horizontal with and a cross-section perpendicular to a longitudinal direction of a balloon portion of a catheter having the shaft for an ablation catheter with a balloon in EXAMPLE 1.

Finally, the operating portion communicating with the guidewire passing lumen 5e and the liquid supplying lumen 6e was attached, and an ablation catheter with a balloon (hereinafter referred to as EXAMPLE 1 catheter) was completed. FIG. 10 shows its balloon portion 1e.

The area of the liquid supplying lumen region of EXAMPLE 1 catheter was 2.01 mm$^2$, and La/Li was 1.00.

Example 2

A shaft made of polyurethane having a length of 1000 mm and an outer diameter of 3.2 mm and having a guidewire passing lumen 5f with a cross-section perpendicular to a longitudinal direction of the shaft being a circle having a diameter of 1.1 mm and a liquid supplying lumen 6f with a cross-section perpendicular to the longitudinal direction of the shaft being a circle having a diameter of 1.8 mm was prepared by extrusion molding to obtain a shaft for an ablation catheter with a balloon 2f.

Figure 11:
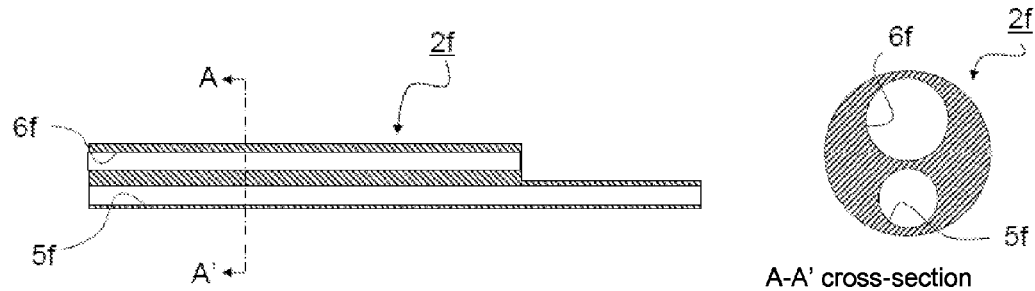
FIG. 11 is a schematic view showing a cross-section horizontal with and a cross-section perpendicular to a longitudinal direction of a front portion of a shaft for an ablation catheter with a balloon in EXAMPLE 2.

A part of a range including the liquid supplying lumen 6f of the shaft for an ablation catheter with a balloon 2f from a front end of the shaft for an ablation catheter with a balloon 2f to a position 40 mm distanced in length from the front end was cut off to have the shape of the front portion shown in FIG. 11.

A copper wire plated with silver and undergoing FEP coating having a length of 1300 mm and a diameter of 0.72 mm was used as the lead wire 8, and a constantan wire undergoing FEP coating having a length of 1300 mm and a diameter of 0.29 mm was used as the temperature sensor lead wire 9.

The coat in a 150 mm range in length from one tip of the lead wire 8 was stripped away, the coat in a 3 mm range in length from one tip of the temperature sensor lead wire 9 was stripped away, and the tips from which the coats were stripped away were overlapped in a range of 1 mm in length of each wire and were fixed by soldering.

The temperature sensor lead wire 9 was inserted into the liquid supplying lumen 6f, and the fixed part of the tips of the lead wire 8 and the temperature sensor lead wire 9 was placed at a position 20 mm distanced in length from the front end of the shaft for an ablation catheter with a balloon 2f. With the position set as a starting point, the lead wire 8 was directly wound around the shaft for an ablation catheter with a balloon 2f and the temperature sensor lead wire 9 in a proximal direction of the ablation catheter with a balloon to form a coiled shape having a length in the longitudinal direction of 10 mm and use it as the electrode-cum-temperature sensor 21.

A remainder of the lead wire 8 after its part was formed in the coiled shape was inserted into the liquid supplying lumen 6f along the temperature sensor lead wire 9.

The balloon 3 made of polyurethane formed in a spherical shape having a diameter of 25 mm and a thickness of 40 μm and having at both ends neck portions one having a length of 15 mm and an inner diameter of 3.2 mm and the other having a length of 15 mm and an inner diameter of 1.6 mm was prepared by dipping.

The neck portion of the balloon 3 having an inner diameter of 3.2 mm was thermally welded on an outer circumference of the front portion of the shaft for an ablation catheter with a balloon 2f, and the neck portion of the balloon 3 having an inner diameter of 1.6 mm was thermally welded so that the liquid supplying lumen 6f of the shaft for an ablation catheter with a balloon 2f would communicate with the interior of the balloon 3.

Figure 12:
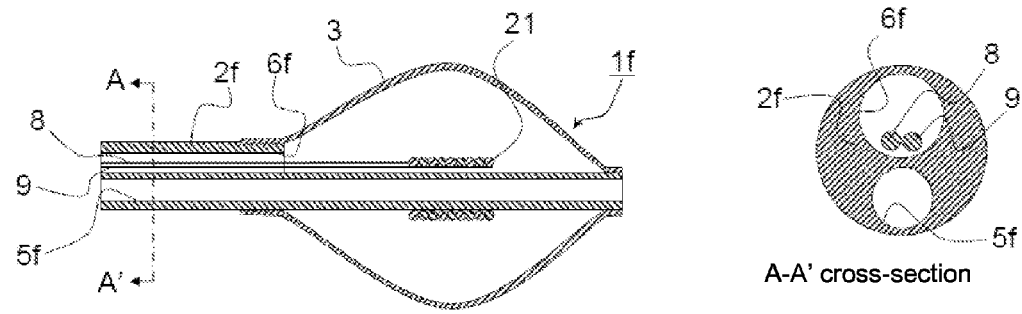
FIG. 12 is a schematic view showing a cross-section horizontal with and a cross-section perpendicular to a longitudinal direction of a balloon portion of a catheter having the shaft for an ablation catheter with a balloon in EXAMPLE 2.

Finally, the operating portion communicating with the guidewire passing lumen 5f and the liquid supplying lumen 6f was attached, and an ablation catheter with a balloon (hereinafter referred to as EXAMPLE 2 catheter) was completed. FIG. 12 shows its balloon portion 1f.

The area of the liquid supplying lumen region of EXAMPLE 2 catheter was 2.07 mm$^2$, and La/Li was 1.73.

Example 3

A shaft made of polyurethane having a length of 1000 mm and an outer diameter of 3.6 mm and having a guidewire passing lumen 5g with a cross-section perpendicular to a longitudinal direction of the shaft being a circle having a diameter of 1.2 mm and a liquid supplying lumen 6g with a cross-section perpendicular to the longitudinal direction of the shaft being a semicircle having a diameter of 2.7 mm was prepared by extrusion molding to obtain a shaft for an ablation catheter with a balloon 2g.

Figure 13:
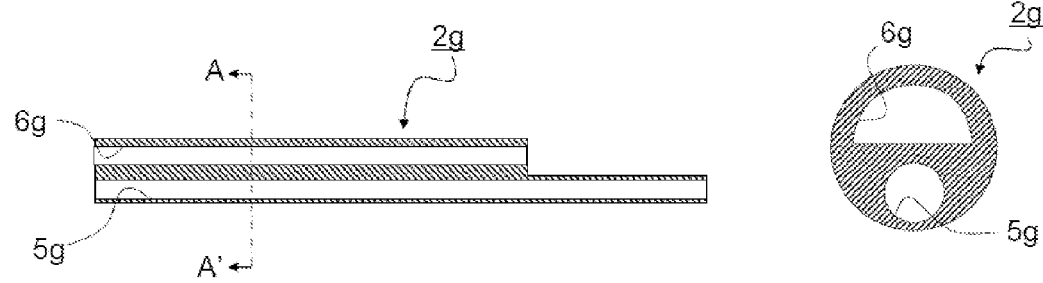
FIG. 13 is a schematic view showing a cross-section horizontal with and a cross-section perpendicular to a longitudinal direction of a front portion of a shaft for an ablation catheter with a balloon in EXAMPLE 3.

A part of a range including the liquid supplying lumen 6g of the shaft for an ablation catheter with a balloon 2g from a front end of the shaft for an ablation catheter with a balloon 2g to a position 40 mm distanced in length from the front end was cut off to have the shape of the front portion shown in FIG. 13.

A copper wire plated with silver and undergoing FEP coating having a length of 1300 mm and a diameter of 0.72 mm was used as the lead wire 8, and a constantan wire undergoing FEP coating having a length of 1300 mm and a diameter of 0.72 mm was used as a temperature sensor lead wire 9g.

The coat in a 150 mm range in length from one tip of the lead wire 8 was stripped away, the coat in a 3 mm range in length from one tip of the temperature sensor lead wire 9g was stripped away, and the tips from which the coats were stripped away were overlapped in a range of 1 mm in length of each wire and were fixed by soldering.

The temperature sensor lead wire 9g was inserted into the liquid supplying lumen 6g, and the fixed part of the tips of the lead wire 8 and the temperature sensor lead wire 9g was placed at a position 20 mm distanced in length from the front end of the shaft for an ablation catheter with a balloon 2g. With the position set as a starting point, the lead wire 8 was directly wound around the shaft for an ablation catheter with a balloon 2g and the temperature sensor lead wire 9g in a proximal direction of the ablation catheter with a balloon to form a coiled shape having a length in the longitudinal direction of 10 mm and use it as the electrode-cum-temperature sensor 21.

A remainder of the lead wire 8 after its part was formed in the coiled shape was inserted into the liquid supplying lumen 6g along the temperature sensor lead wire 9g.

The balloon 3 made of polyurethane formed in a spherical shape having a diameter of 25 mm and a thickness of 40 μm and having at both ends neck portions one having a length of 15 mm and an inner diameter of 3.2 mm and the other having a length of 15 mm and an inner diameter of 1.6 mm was prepared by dipping.

The neck portion of the balloon 3 having an inner diameter of 3.2 mm was thermally welded on an outer circumference of the front portion of the shaft for an ablation catheter with a balloon 2g, and the neck portion of the balloon 3 having an inner diameter of 1.6 mm was thermally welded so that the liquid supplying lumen 6g of the shaft for an ablation catheter with a balloon 2g would communicate with the interior of the balloon 3.

Figure 14:
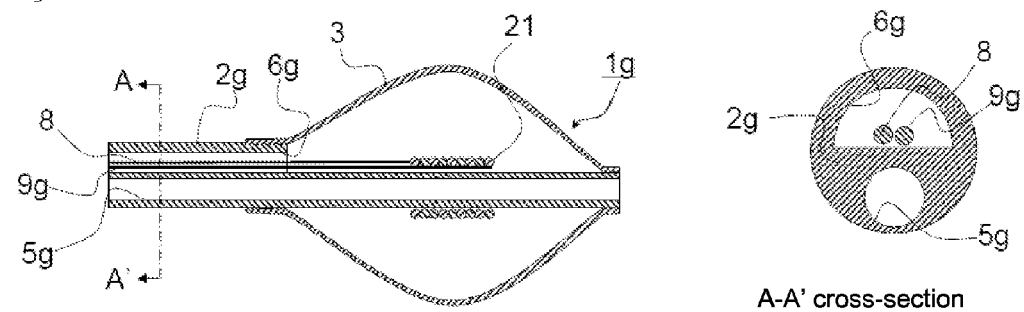
FIG. 14 is a schematic view showing a cross-section horizontal with and a cross-section perpendicular to a longitudinal direction of a balloon portion of a catheter having the shaft for an ablation catheter with a balloon in EXAMPLE 3.

Finally, the operating portion communicating with the guidewire passing lumen 5g and the liquid supplying lumen 6g was attached, and an ablation catheter with a balloon (hereinafter referred to as EXAMPLE 3 catheter) was completed. FIG. 14 shows its balloon portion 1g.

The area of the liquid supplying lumen region of EXAMPLE 3 catheter was 2.05 mm², and La/Li was 2.26.

Comparative Example

A tube made of polyurethane having a length of 960 mm, an outer diameter of 3.2 mm, and an inner diameter of 2.4 mm was prepared as an outer cylinder shaft 22, and a tube made of diamide having a length of 1000 mm, an outer diameter of 1.6 mm, and an inner diameter of 1.2 mm was prepared as an inner cylinder shaft 23.

A copper wire plated with silver and undergoing FEP coating having a length of 1300 mm and a diameter of 0.72 mm was used as the lead wire 8, and a constantan wire undergoing FEP coating having a length of 1300 mm and a diameter of 0.29 mm was used as the temperature sensor lead wire 9.

The coat in a 150 mm range in length from one tip of the lead wire 8 was stripped away, the coat in a 3 mm range in length from one tip of the temperature sensor lead wire 9 was stripped away, and the tips from which the coats were stripped away were overlapped in a range of 1 mm in length of each wire and were fixed by soldering.

The fixed part of the tips of the lead wire 8 and the temperature sensor lead wire 9 was placed at a position 20 mm distanced in length from a front end of the inner cylinder shaft 23. With the position set as a starting point, the lead wire 8 was directly wound around the inner cylinder shaft 23 and the temperature sensor lead wire 9 in a proximal direction of the ablation catheter with a balloon to form a coiled shape having a length in the longitudinal direction of 10 mm and use it as the electrode-cum-temperature sensor 21.

The inner cylinder shaft 23 forming the electrode-cum-temperature sensor 21 at a front portion was inserted into the outer cylinder shaft 22 so that a part of the inner cylinder shaft 23 in a 40 mm range in length from its front end would be projected from the outer cylinder shaft 22.

The balloon 3 made of polyurethane formed in a spherical shape having a diameter of 25 mm and a thickness of 40 μm and having at both ends neck portions one having a length of 15 mm and an inner diameter of 3.2 mm and the other having a length of 15 mm and an inner diameter of 1.6 mm was prepared by dipping.

A front portion of the balloon 3 was thermally welded on an outer circumference of the front portion of the inner cylinder shaft 23, and a rear portion of the balloon 3 was thermally welded on an outer circumference of a front portion of the outer cylinder shaft 22.

Figure 15:
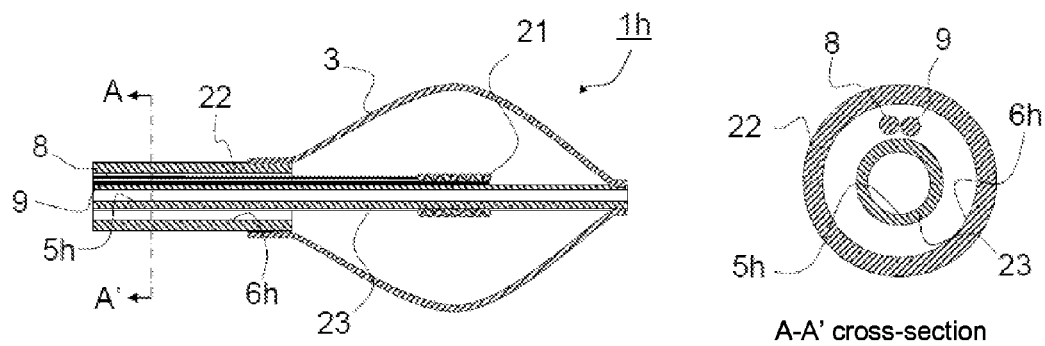
FIG. 15 is a schematic view showing a cross-section horizontal with and a cross-section perpendicular to a longitudinal direction of a balloon portion of a catheter having a shaft for an ablation catheter with a balloon in COMPARATIVE EXAMPLE.

Finally, the operating portion communicating with a guidewire passing lumen 5h and a liquid supplying lumen 6h was attached, and an ablation catheter with a balloon (hereinafter referred to as COMPARATIVE EXAMPLE catheter) was completed. FIG. 15 shows its balloon portion 1h.

The area of the liquid supplying lumen region of COMPARATIVE EXAMPLE catheter was 2.04 mm², and La/Li was 3.11.

(Deflating Test)

A deflating operation was conducted for each of the ablation catheters with a balloon prepared in EXAMPLES 1 to 3 and COMPARATIVE EXAMPLE, and the number of times of operation until no remaining air existed was compared.

A sequence of procedures of supplying the entirety of a 30 mL mixed solution of a contrast medium (Hexabrix 320) and 0.9% saline (volume ratio 1:1) collected in a syringe to the interior of the balloon and the like via the operating portion and discharging air or the mixed solution to the syringe until the interior of the balloon in a positive pressure state was returned to a normal pressure state was counted as a single deflating operation.

According to the result of the deflating test, the number of times of the deflating operation of EXAMPLE 1 catheter was once, and the operating time was 15 seconds. Also, the number of times of the deflating operation of EXAMPLE 2 catheter was twice, and the number of times of the deflating operation of EXAMPLE 3 catheter was 4 times. On the other hand, in COMPARATIVE EXAMPLE catheter, air remained in the interior of the balloon and the like even after 10 times of the deflating operation.

As is apparent from the result of the deflating test, the ablation catheter with a balloon having the shaft for an ablation catheter with a balloon according to embodiments of the present invention enables complete deflation and prevents the possibility of mixing of air in the blood vessel of the patient even in a case where the balloon is damaged during the treatment to assure sufficient safety.

(In-Shaft Water Pressure Test)

Water having a predetermined flow rate was made to pass through each of the shafts of the ablation catheters with a balloon prepared in EXAMPLES 1 to 3 and COMPARATIVE EXAMPLE with use of a roller pump to measure and compare water pressure in the shaft.

Figure 16:
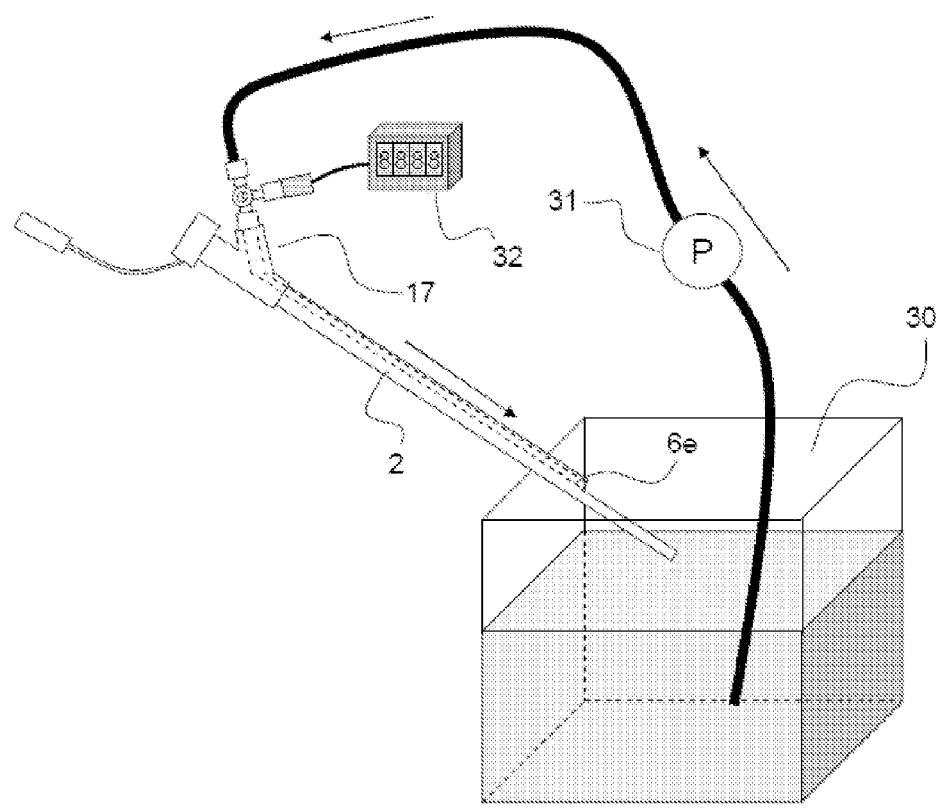
FIG. 16 is a schematic view of an in-shaft water pressure testing system.

FIG. 16 is a schematic view of an in-shaft water pressure testing system (a test example of the ablation catheter with a balloon having the shaft for an ablation catheter with a balloon 2). The front end of each of the shafts of the ablation catheters with a balloon prepared in EXAMPLES 1 to 3 and COMPARATIVE EXAMPLE to which no balloon was attached was immersed into water in a water tank 30. The bifurcated connector 17 was connected to the operating portion to communicate with the liquid supplying lumen or a space between the inner cylinder shaft and the outer cylinder shaft. To the bifurcated connector 17 were connected a roller pump 31 and a pressure gauge 32. Water pumped up from the water tank 30 with use of the roller pump 31 was supplied via the operating portion at a flow velocity of 10 mL/second to pass through the liquid supplying lumen or the space between the inner cylinder shaft and the outer cylinder shaft, and a value of the pressure gauge 32 at that time was read off.

According to the result of the in-shaft water pressure test, the water pressure of EXAMPLE 1 catheter was 77 kPa, the water pressure of EXAMPLE 2 catheter was 92 kPa, and the water pressure of EXAMPLE 3 catheter was 106 kPa, but the water pressure of COMPARATIVE EXAMPLE catheter was 132 kPa.

As is apparent from the result of the in-shaft water pressure test, the shaft for an ablation catheter with a balloon according to embodiments of the present invention is shaped to allow the liquid such as saline to pass therethrough more smoothly and to improve the mixing efficiency, which leads to quick uniforming of the surface temperature of the balloon and suppression of remaining air.

(Balloon Surface Temperature Test)

Each electrode 4 of the ablation catheters with a balloon prepared in EXAMPLES 1 to 3 and COMPARATIVE EXAMPLE was supplied with radio-frequency power by the radio-frequency generator to compare the surface temperatures of upper and lower ends of the balloon.

Figure 17:
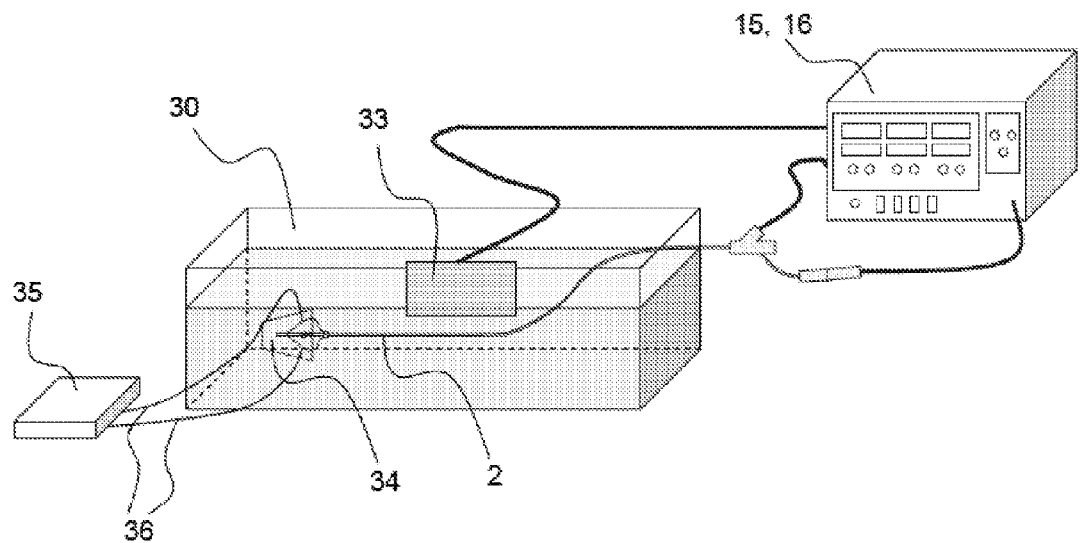
FIG. 17 is a schematic view of a balloon surface temperature testing system.
Figure 18:
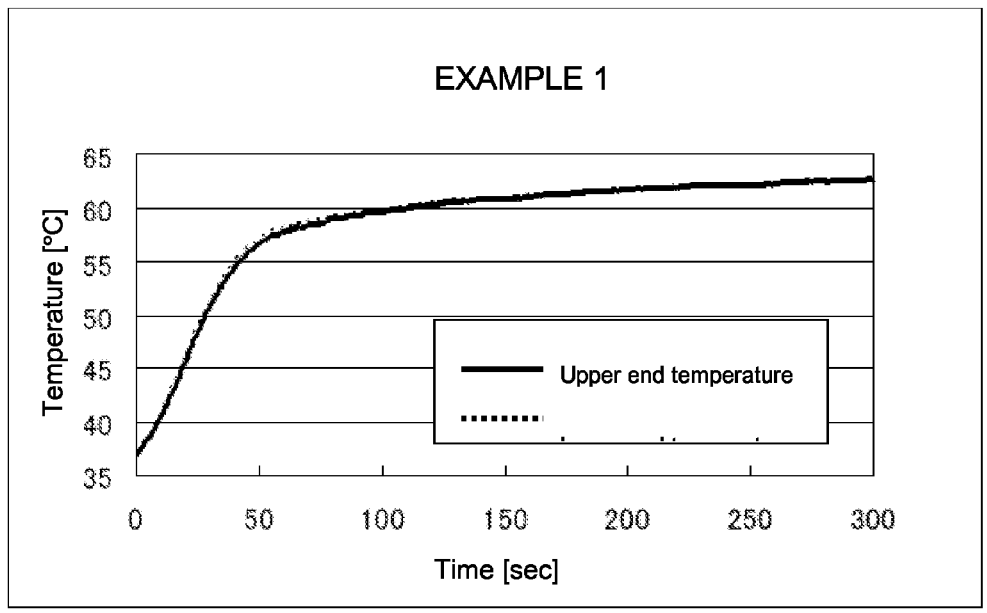
FIG. 18 is a graph showing recorded surface temperatures of upper and lower ends of a balloon of the catheter having the shaft for an ablation catheter with a balloon in EXAMPLE 1.
Figure 19:
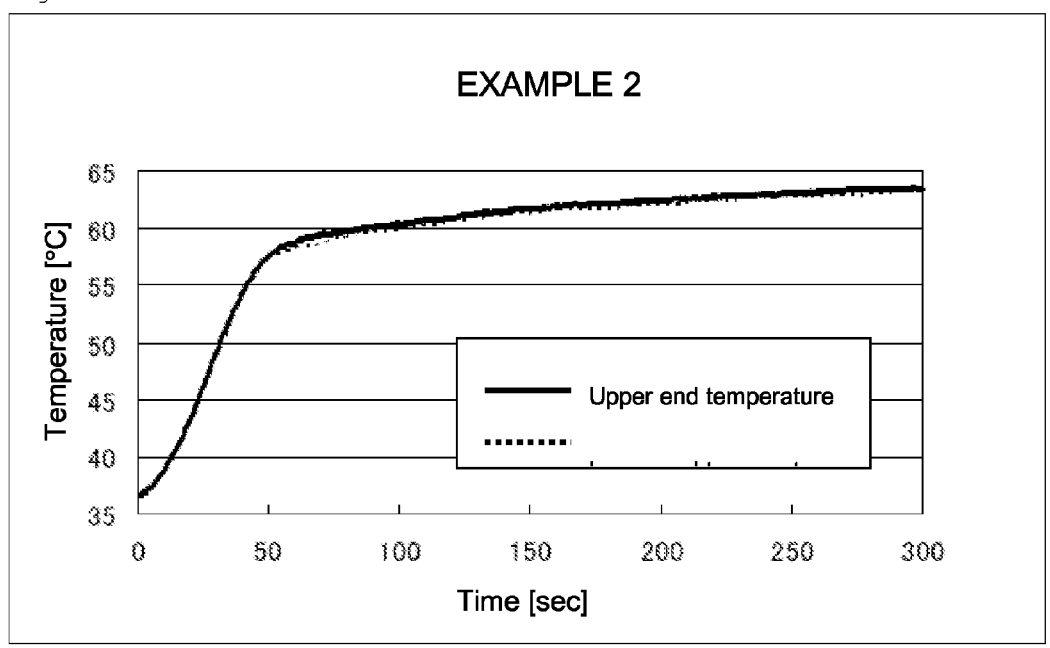
FIG. 19 is a graph showing recorded surface temperatures of upper and lower ends of a balloon of the catheter having the shaft for an ablation catheter with a balloon in EXAMPLE 2.
Figure 20:
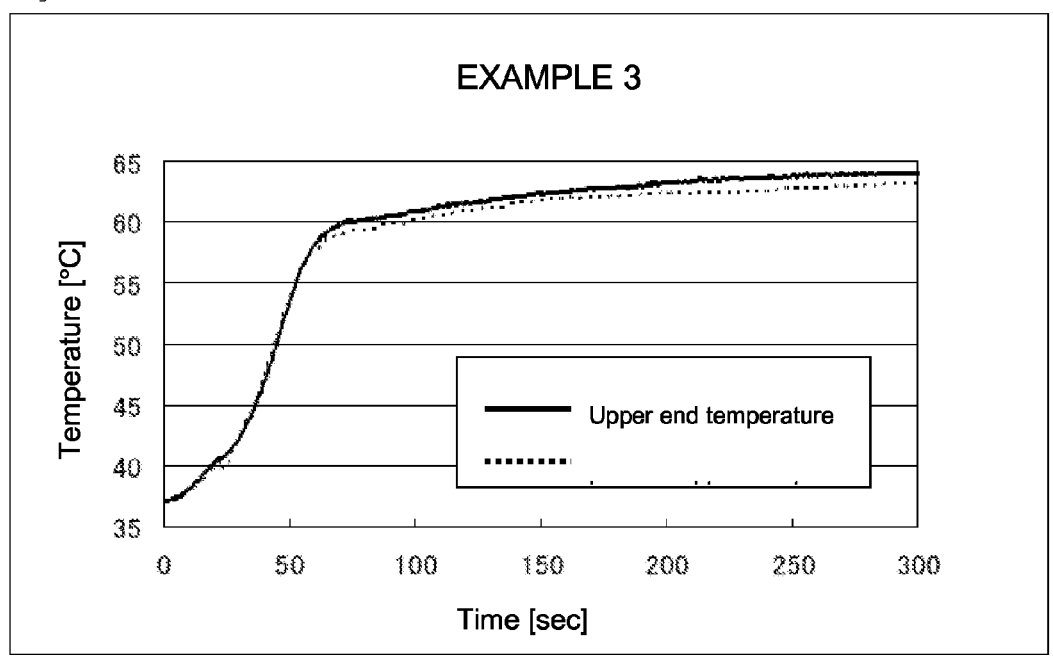
FIG. 20 is a graph showing recorded surface temperatures of upper and lower ends of a balloon of the catheter having the shaft for an ablation catheter with a balloon in EXAMPLE 3.
Figure 21:
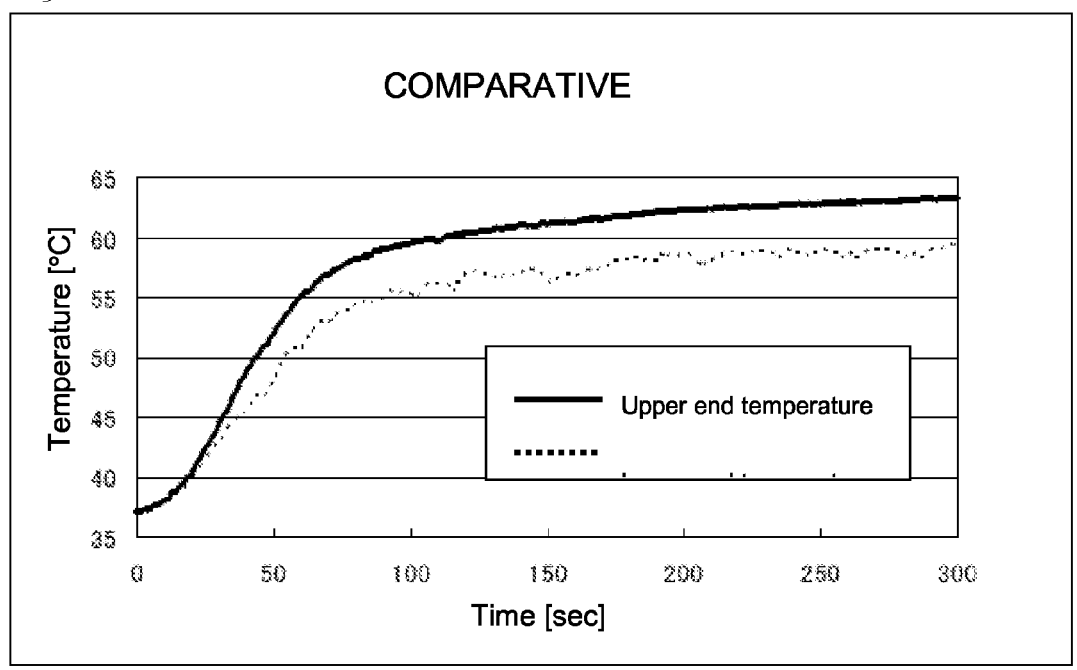
FIG. 21 is a graph showing recorded surface temperatures of upper and lower ends of a balloon of the catheter having the shaft for an ablation catheter with a balloon in COMPARATIVE EXAMPLE.

FIG. 17 is a schematic view of a balloon surface temperature testing system. The radio-frequency generator 15 (one into which the mixing generator 16 has been integrated) was connected to a counter electrode plate 33 attached to an inner wall of the water tank 30, and the water tank 30 was filled with 35 L 0.9% saline at 37° C.

A pseudo affected tissue 34 made of agar into a shape in which the balloon expanded so that the maximum diameter thereof might be 25 mm would be fit was installed in the water tank 30 so as to be immersed completely in the 0.9% saline, thermocouples 36 were respectively arranged at an upper end and a lower end in a vertical direction of an outline contacted by an outer circumference of a maximum diameter of the balloon 3 expanded so that the maximum diameter thereof might be 25 mm, and the thermocouples 36 were connected to a temperature data logger 35.

Each of EXAMPLE 1 catheter, EXAMPLE 2 catheter, EXAMPLE 3 catheter, and COMPARATIVE EXAMPLE catheter was connected to the radio-frequency generator 15 and the mixing generator 16 and was immersed into the 0.9% saline in the water tank 30, the balloon 3 was expanded by a mixed solution of a contrast medium (Hexabrix 320) and 0.9% saline (volume ratio 1:1) so that the maximum diameter thereof might be 25 mm, and each catheter was fit into the pseudo affected tissue 34.

At the same time as starting supplying radio-frequency power (frequency: 1.8 MHz, maximum power: 150 W, and setting temperature: 70° C.) by the radio-frequency generator 15, the liquid in the balloon and the like was vibrated and mixed by the mixing generator 16 at a volume per single supply/discharge of 0.4 mL and at a vibration frequency of 1 Hz.

For 5 minutes from the beginning to the end of supply of the radio-frequency power, the surface temperatures of the upper and lower ends of the balloon were recorded at a sampling period of 1 second by the temperature data logger 35.

The recorded surface temperatures of the upper and lower ends of the balloons of EXAMPLE 1 catheter, EXAMPLE 2 catheter, EXAMPLE 3 catheter, and COMPARATIVE EXAMPLE catheter are shown in FIGS. 18, 19, 20, and 21, respectively.

An average value of a surface temperature difference between the upper end temperature and the lower end temperature of the balloon in EXAMPLE 1 catheter during supply of the radio-frequency power was 0.2° C., the average value in EXAMPLE 2 catheter was 0.4° C., and the average value in EXAMPLE 3 catheter was 0.8° C. Also, a period of time from a time point when the surface temperature of one of the upper and lower ends of the balloon exceeded 60° C., which is an optimal temperature for ablation for treatment of an atrial fibrillation, to a time point when the surface temperature of the other exceeded 60° C. during supply of the radio-frequency power to EXAMPLE 1 catheter was 6 seconds, the period in the case of EXAMPLE 2 catheter was 15 seconds, and the period in the case of EXAMPLE 3 catheter was 26 seconds.

On the other hand, the average value of the surface temperature difference between the upper end temperature and the lower end temperature of the balloon in COMPARATIVE EXAMPLE catheter during supply of the radio-frequency power was 3.6° C. Also, during supply of the radio-frequency power to COMPARATIVE EXAMPLE catheter, the temperature of the upper end of the balloon exceeded 60° C., but the temperature of the lower end of the balloon was not stable and did not exceed 60° C. Further, the surface temperature difference between the upper end temperature and the lower end temperature of the balloon tended to be large as time passed.

As is apparent from the result of the balloon surface temperature test, the shaft for an ablation catheter with a balloon according to embodiments of the present invention can uniform the surface temperature of the balloon quickly, which leads to decrease in burden on the patient and improvement in treatment accuracy.

The present invention can be used as a shaft for an ablation catheter with a balloon for ablation of a target lesion location.

DESCRIPTION OF REFERENCE SIGNS

1, 1*a*, 1*c*, 1*e*, 1*f*, 1*g*, 1*h* . . . balloon portion of an ablation catheter with a balloon, 2, 2*a*, 2*b*, 2*c*, 2*d*, 2*e*, 2*f*, 2*g* . . . shaft for an ablation catheter with a balloon, 3 . . . balloon, 4 . . . electrode, 5*a*, 5*b*, 5*c*, 5*d*, 5*e*, 5*f*, 5*g*, 5*h* . . . guidewire passing lumen, 6*a*, 6*b*, 6*c*, 6*d*, 6*e*, 6*f*, 6*g*, 6*h* . . . liquid supplying lumen, 7 . . . temperature sensor, 8 . . . lead wire, 9, 9*g* . . . temperature sensor lead wire, 10*a*, 10*b* . . . tube, 11 . . . embedded tube, 12 . . . outer cylinder shaft, 13 . . . operating portion, 14 . . . guidewire, 15 . . . radio-frequency generator, 16 . . . mixing generator, 17 . . . bifurcated connector, 18 . . . infusion pump, 19 . . . ablation catheter system with a balloon, 20 . . . third lumen, 21 . . . electrode-cum-temperature sensor, 22 . . . outer cylinder shaft, 23 . . . inner cylinder shaft, 30 . . . water tank, 31 . . . roller pump, 32 . . . pressure gauge, 33 . . . counter electrode plate, 34 . . . pseudo affected tissue, 35 . . . temperature data logger, 36 . . . thermocouple

The invention claimed is:
1. An ablation catheter system comprising:
a shaft of an ablation catheter with a balloon fixed to a front side of the shaft,
an electrode configured to heat the balloon, and
a mixing generator arranged outside of the balloon and configured to vibrate and mix a heating liquid, wherein the shaft is formed of a single pipe comprising first and second lumens, the first lumen is a guidewire passing lumen configured to allow a guidewire to pass therethrough, the second lumen is a liquid supplying lumen configured to supply the vibrated and mixed heating liquid to an interior of the balloon, and at least one lead wire and a temperature sensor lead wire arranged in the liquid supplying lumen, wherein the liquid supplying lumen is configured to have a ratio of (La/Li) or 1 to 2.3, wherein a length (La) of an outline of a cross-sectional shape of the liquid supplying lumen in a cross-section perpendicular to a longitudinal direction of the single pipe is a sum of the inner circumference of the liquid supplying lumen and outer circumference of each lead wire and the temperature sensor lead wire, wherein a length (Li) is equal to a circumference of a circle having an area equal to a cross-sectional area of the liquid supplying lumen surrounded by the outline, and wherein the cross-sectional area of the liquid supplying lumen is 2.0 to 4.5 mm$^2$.

2. The ablation catheter system according to claim 1, wherein the ratio (La/Li) is 1 to 1.8.

* * * * *